(12) United States Patent
Musha et al.

(10) Patent No.: US 6,303,802 B1
(45) Date of Patent: Oct. 16, 2001

(54) PROCESS FOR THE PREPARATION OF ACYLOXYALKANESULFONIC ACIDS

(75) Inventors: Kiyoshi Musha; Kazuhiko Hayashi, both of Tokyo (JP)

(73) Assignee: Asahi Denka Kogyo K.K., Tokyo (JP)

( * ) Notice: Subject to any disclaimer, the term of this patent is extended or adjusted under 35 U.S.C. 154(b) by 0 days.

(21) Appl. No.: 09/319,254

(22) PCT Filed: Dec. 5, 1997

(86) PCT No.: PCT/JP97/04467

§ 371 Date: Jun. 9, 1999

§ 102(e) Date: Jun. 9, 1999

(87) PCT Pub. No.: WO98/25891

PCT Pub. Date: Jun. 18, 1998

(30) Foreign Application Priority Data

Dec. 9, 1996 (JP) .................................................. 8-328716

(51) Int. Cl.⁷ ......................................................... C11D 1/28

(52) U.S. Cl. .............................. 554/92; 516/198; 516/200
(58) Field of Search ............................... 554/92; 516/198, 516/200

(56) References Cited

U.S. PATENT DOCUMENTS 5,523,432 * 6/1996 Raths et al. ........................... 554/92

FOREIGN PATENT DOCUMENTS 2-1454 * 1/1990 (JP) .

* cited by examiner

*Primary Examiner*—Deborah D. Carr
(74) *Attorney, Agent, or Firm*—Oblon, Spivak, McClelland, Maier & Neustadt, P.C.

(57) ABSTRACT

A fatty acid and/or an alkyl ester of a fatty acid and isethionic acid are allowed to react at a temperature of not more than 130° C. The present invention provides a process for preparing a fatty ester of isethionic acid or a salt thereof exhibiting an ameliorated hue and smell and in which few by-products are produced.

33 Claims, No Drawings

PROCESS FOR THE PREPARATION OF ACYLOXYALKANESULFONIC ACIDS

This application is a 371 of PCT/JP97/04467 filed on Dec. 5, 1997.

FIELD OF THE INVENTION

The present invention relates to a process for preparing an acyloxy alkanesulfonic acid and a salt thereof. More specifically, the invention relates to a process for preparing an acyloxy alkanesulfonic acid and a salt thereof wherein the acyloxy alkanesulfonic acid can be prepared under mild conditions.

DESCRIPTION OF THE RELATED ART

Sodium salts of fatty esters of hydroxy alkanesulfonic acids such as isethionic acid (2-hydroxy ethanesulfonic acid) have far stronger resistance to hard water than soap, are mild to the skin and provide lather with a rich body. They are also relatively thermoplastic when used as a material for molding synthesized soaps or composite soaps. Due to these characteristics, they have been used for a long time as materials for producing synthesized soaps or composite soaps, components of shampoos and body cleaning agents, fiber scouring agents or coloring aids and the like.

According to "HAPPI, 92, 1995", PPG Industries, Inc. discovered that at room temperature the water solubility of a salt of a coconut oil fatty ester of isethionic acid was improved by 30% by changing the counter ion thereof from a sodium ion to an ammonium ion, and introduced the salt as an active agent which was mild, environmentally friendly and had good lathering qualities. Generally, ammonium salts are known to have a water solubility higher than that of sodium salts. However, there is a disclosure that the difference brought about by the ammonium salt of the coconut oil fatty ester of isethionic acid is unprecedentedly large, that this salt has low peroral toxicity and is considered to be almost innoxious, and that its biodegradability exceeds the OECD 301D guide lines, i.e. 65% in 15 days. Therefore, this substance is a surfactant with great promise.

These salts of acyloxy alkanesulfonic acids, such as salts of fatty esters of isethionic acid are typically prepared as follows, where isethionic acid is used as a representative example.

One such method is a process in which isethionic acid is allowed to directly react with a fatty acid (U.S. Pat. No. 3,151,136, Japanese Patent Laid-open No.2-1454). In another method, a salt of isethionic acid produced in any process, for example, from a hydrogen sulfite such as sodium hydrogen sulfite or ammonium hydrogen sulfite and ethylene oxide, is esterified with a fatty acid (hereinafter referred to as a direct esterification method).

In the above-mentioned U.S. Pat. No. 3,151,136, a fatty acid is heated to 100–120° C. under a reduced pressure, isethionic acid is then added thereto and the mixture is maintained at 110° C., and then at 135° C. to complete the esterification reaction. In the Japanese Patent Laid-open No.2-1454 discloses that isethionic acid and a fatty acid are reacted at 110–120° C., then after-stirring is carried out at 135° C.

In Japanese Patent Laid-open No.2-1454, sodium salt of a fatty ester of isethionic acid is produced from such materials as coconut oil fatty acid and isethionic acid. However, impurities are yielded as the reaction is carried out at a maximum temperature of up to 135° C., and the obtained salt of the fatty ester of isethionic acid has low purity and shows deteriorated water solubility. This does not present a problem for a salt such as a sodium salt which is not required to have high water solubility, but for a salt which is required to have high water solubility, this process is not practical.

Other examples employing the direct esterification method are given, for example, in WO 95/01331 and WO 95/11957 wherein a process in which ammonium isethionate is produced from ammonium hydrogen sulfite and ethylene oxide is described, and the obtained ammonium isethionate is used together with coconut oil fatty acid to produce an ammonium salt of coconut oil fatty ester of isethionic acid. In such a direct esterification process, although sodium chloride is not a by-product, the reaction requires a temperature as high as almost 200° C., which results in yielding by-products, deterioration of hue and generation of bad smell. Dehydration is carried out for the esterification reaction, however, as a lot of foaming occurs under a reduced pressure, the reaction takes a long time and a reaction vessel having a large capacity in relation to the amount of the product must be employed. There is no improvement on this point in the process shown in WO 95/01331 and WO 95/11957, since the main points thereof are to decrease the amount of impurities such as ethylene glycol during the production of salts of isethionic acid.

An alternative method is a process in which an obtained isethionate salt and a fatty acid chloride are allowed to react to produce a fatty ester of isethionic acid (hereinafter referred to as acid chloride method). In this acid chloride method, the product can be obtained at a relatively low temperature of not more than about 100° C., however, sodium chloride is disadvantageously by-produced.

Furthermore, there is still another method in which an obtained isethionate salt and a methyl ester of a fatty acid are subjected to an ester exchange reaction (hereinafter referred to as ester exchange method). In this ester exchange method, again, a temperature as high as about 200° C. is required for the reaction, therefore the problems of by-products, deteriorated hue and generation of smell exist. This process is less advantageous from the view point of cost and ease of operation, since the production of a methyl ester of a fatty acid is inevitable.

The sodium salt of coconut oil fatty ester of isethionic acid has limited uses due to its low water solubility, as an anionic surfactant, of up to several % at room temperature. Although the ammonium salt has relatively superior water solubility, it has a problem in that it smells at higher pH ranges. Therefore, a salt of a fatty ester of isethionic acid having the same or a higher level of water solubility and lathering properties has been desired. The industrially available hydrogen sulfite salts are more or less limited to sodium and ammonium salts, and since the counter ion is not displaced in the production of an isethionate from a hydrogen sulfite salt and ethylene oxide or in the direct esterification of an isethionate and a fatty acid, the types of counter ions of the fatty ester of isethionic acid are more or less limited to sodium and ammonium. In order to produce a salt of a desired type, a sodium salt or ammonium salt of a fatty ester of isethionic acid must be subjected to an ester exchange reaction and the like to be converted into the desired salt, thus it is not easy to industrially produce various salts. Once a fatty ester of isethionic acid is obtained, it can be neutralized with a desired counter base to industrially produce various kinds of salts easily, and there is no need for an ester exchange reaction. Therefore, development of a process for preparing the fatty ester of isethionic acid has been long desired.

The purpose of the present invention is to provide a process of preparing an acyloxy alkanesulfonic acid or a salt thereof having excellent solubility in polar solvents, and salts of various counter ions which can be easily produced therewith, wherein reaction is carried out under mild conditions. Accordingly, few by-products are yielded, the hue and smell are ameliorated, there is little foaming and dehydration of the reaction system under a reduced pressure can be easily carried out so that the reaction time can be shortened, to provide a polar solvent solution of the salt of the acyloxy alkanesulfonic acid.

SUMMARY OF THE INVENTION

In one aspect of the present invention, a process for preparing an acyloxy alkanesulfonic acid from a fatty acid and/or an alkyl ester of a fatty acid and a hydroxy alkylsulfonic acid is provided in which, an esterification reaction is carried out between the fatty acid and/or the alkyl ester of the fatty acid and the hydroxy alkylsulfonic acid at a maximum temperature of not more than 130° C.

In another aspect of the present invention, there is provided a process for preparing a salt of acyloxy alkanesulfonic acid in which the acyloxy alkanesulfonic acid obtained by the above-mentioned process is allowed to react with a base.

In a further aspect of the present invention, there is provided a surfactant comprising a salt of an acyloxy alkanesulfonic acid obtained by the above-mentioned process.

In yet a further aspect of the present invention, there is provided a polar solvent solution, emulsion, or dispersion of a salt of an acyloxy alkanesulfonic acid obtained by the above-mentioned processes.

BEST MODE FOR CARRYING OUT THE INVENTION

According to the present invention, a hydroxy alkyl group having 2–4 carbon atoms is suitable as the hydroxy alkyl group of the hydroxy alkylsulfonic acid, and in particular, the best effect can be obtained when the hydroxy alkylsulfonic acid is 2-hydroxy ethanesulfonic acid (isethionic acid). Accordingly, the present invention will be explained using isethionic acid as a representative example.

The process for preparing isethionic acid used as a raw material is not particularly limited. For example, U.S. Pat. No. 4,910,330 discloses a process in which mercaptoethanol is oxidized, Japanese Patent Laid-opn No.4-275,270 discloses a process in which sodium salt of isethionic acid is produced from sodium hydrogen sulfite and ethylene oxide, and sodium is then removed by electrodialysis, U.S. Pat. No. 4,499,028 discloses a process in which dried sodium salt of isethionic acid is allowed to react with concentrated hydrochloric acid, U.S. Pat. No. 4,696,773 discloses a process in which isethionic acid is produced from a sodium salt of isethionic acid, hydrochloric acid and ethanol, U.S. Pat. No. 5,053,530 discloses a process in which a sodium salt of isethionic acid and oxalic acid are allowed to react, and Japanese Patent Laid-open No.3-66659 discloses a process in which isethionic acid is obtained from a sodium salt of isethionic acid, hydrochloric acid and ethanol. At present, a process in which mercaptoethanol is oxidized with hydrogen peroxide is advantageous as it is an inexpensive process.

The presence of a compound such as ethylene glycol, which produces a water-insoluble product when esterified with a fatty acid will undesirably decrease the water solubility of a salt of a fatty ester of isethionic acid and increase the clarifying temperature. In a process wherein mercaptoethanol is oxidized, oxidized intermediates such as 2,2'-dithiodiethanol and a sulphoxide in which the S—S bond is retained and oxygen is added present problems, and this content is preferably not more than 1% based on a 70% aqueous solution of isethionic acid. When oxidizing mercaptoethanol, the use of an excess amount of an oxidizing agent for complete oxidation treatment can reduce the amount of impurities. In addition, these by-products can be removed and the product can be refined by ion-exchange treatment, adsorbing treatment, oxidation treatment, distillation, stripping and the like. For example, stripping can be carried out by blowing nitrogen gas at 50–100° C. under 10–30 mmHg.

For preparing a salt of a fatty ester of isethionic acid, either isethionic acid alone or a mixture of isethionic acid and a salt of isethionic acid can be used. The higher the ratio of the salt of isethionic acid in the mixture of isethionic acid and the salt of isethionic acid becomes, the higher the temperature required for esterification reaction becomes. Thus, in order to attain the object of the present invention it is desirable that the ratio of the salt of isethionic acid is not more than 70%. Further, a replacement of the counter ion does not occur, the type of counter ion of the isethionate is decided depending upon which type of isethionic acid fatty ester salt is desired.

A salt of isethionic acid can be obtained by partial neutralization of isethionic acid with a base. The counter ion of the base used is not particularly limited. For example bases in which an alkali metal ion (sodium, potassium, lithium and the like), alkaline earth metal ion (magnesium, calcium and the like), ammonium ion, alkanolamine ion (ethanolamine, diethanolamine, triethanolamine, isopropanolamine, diisopropanolamine, triisopropanolamine and ethylenediaminetetra(propyleneglycol) and the like) are counter ions can be used. The concentration and amount of the base are not particularly limited. A salt of isethionic acid can also be synthesized from a hydrogen sulfite salt and ethylene oxide.

The fatty acid can be either a saturated or unsaturated fatty acid. The number of carbon atoms of the fatty acid is 6–22, particularly preferably 8–18. Examples include coconut oil fatty acid, palm kernel oil fatty acid, lauric acid, oleic acid, stearic acid, isostearic acid and the like. An alkyl ester of a fatty acid can be an alkyl ester of either a saturated or unsaturated fatty acid. The number of carbon atoms of the fatty acid is 6–22, particularly preferably 8–18. Examples include coconut oil fatty acid, palm kernel oil fatty acid, lauric acid, oleic acid, stearic acid, isostearic acid and the like. The alkyl group bonded thereto by ester linkage is not particularly limited, and methyl or ethyl group can be used.

The molar ratio of a fatty acid and/or an alkyl ester of a fatty acid to the isethionic acid and/or a salt thereof charged for esterification is preferably 0.95–1.1. If this ratio is more than 1.1, a fatty acid and/or an alkyl ester of the fatty acid is left after esterification or a water insoluble esterified compound is produced, resulting in a decrease in the water solubility of the neutralized salt and an increase in the clarifying temperature of the aqueous solution. If the ratio is less than 0.95, the esterification is incompletely carried out and this is disadvantageous.

Although a catalyst is not usually required for esterification of isethionic acid and/or a salt thereof and a fatty acid and/or an alkyl ester of a fatty acid, previously adding a fatty ester of isethionic acid and/or a salt thereof is preferable, because the reaction time can be shortened.

Since the isethionic acid and/or a salt thereof are typically obtained in the form of an aqueous solution, in the initial stage of the esterification of the isethionic acid and/or a salt thereof and a fatty acid and/or an alkyl ester of a fatty acid, they are not mutually soluble and a two phase non-homogeneous reaction is carried out, and the system becomes homogeneous as the reaction progresses and a fatty ester of isethionic acid or a salt thereof is generated. When an appropriate amount of a fatty ester of isethionic acid or a salt thereof is added prior to esterification, the system becomes homogeneous from the initial stage of the reaction and the reaction time can be advantageously shortened. The amount of the fatty ester of isethionic acid or a salt thereof to be added is preferably 5–20% of the total amount of the isethionic acid and/or the salt thereof and the fatty acid and/or the alkyl ester of the fatty acid. If the amount is smaller than this range a homogeneous system cannot be provided, while an amount greater than this range is disadvantageous in terms of cost. The esterification reaction is progressed by heating the charged mixture of isethionic acid and/or the salt thereof and the fatty acid and/or the alkyl ester of the fatty acid to the reaction temperature followed by dehydration under a reduced pressure.

The reaction temperature is 50–130° C., preferably 60–120° C. A reaction temperature higher than this range is unnecessary or even undesirable due to side reactions, staining or smell. At a temperature lower than this range, the reaction rate is slowed or the reaction does not proceed. Throughout the entire esterification reactions, the maximum temperature is not more than 130° C., preferably less than 100° C. At a temperature higher than this, side reaction, staining or a smell occurs and the object of the present invention cannot be achieved. According to the process of the present invention, the reaction can be carried out at a low temperature and this is thought to be because the isethionic acid itself works as a catalyst.

According to the present invention, reduction of the pressure is not very restricted as little foaming occurs. Therefore, the water generated by esterification or the water existed as the solvent can be removed quicker and under a reduced pressure lower than the conventional process. Accordingly, the reaction can be completed in a shorter time than with the conventional process, and more importantly, the generation of by-products is controlled and a fatty ester of isethionic acid having better water solubility than that of the conventional process can be obtained.

According to the present invention, an esterification reaction rate of 90% or higher can be achieved as shown in the Examples.

When producing a salt of a fatty ester of isethionic acid, the product is allowed to react with a desired base after the esterification. In such an event, the produced ester is hydrolyzed if it is contacted with water in an acid or alkaline condition at a high temperature and for a long period of time, and since the polar solvent solution becomes turbid and the clarifying temperature is increased, it is preferable that a polar solvent solution of the base be added and the solution be stirred so that a high pH region is not locally generated. The polar solvent is not particularly limited. For example, water, lower alcohols, glycols, and glycerin or a mixture thereof can be used. The final pH is adjusted to 6–8, preferably to 6.5–7.0 in order to prevent hydrolysis of the ester linkage.

The counter ion of the base used is not particularly limited. For example, bases in which an alkali metal ion (sodium, potassium, lithium and the like), alkaline earth metal ion (magnesium, calcium and the like), ammonium ion, alkanolamine ion (ethanolamine, diethanolamine, triethanolamine, isopropanolamine, diisopropanolamine, triisopropanolamine and ethylenediaminetetra (propyleneglycol) and the like) are counter ions, can be used. An alkanolamine salt obtained from the base in which alkanolamine is contained as the counter ion shows much better blending properties, lathering properties, water solubility, and sensation upon use than those of sodium salt and ammonium salt. In particular, the alkanolamine salt has good water solubility and its viscosity in aqueous solution is much lower than that of the ammonium salt. Further, it has good blending properties with other active agents. The viscosity of the aqueous solution of the alkanolamine is increased by addition of a sodium compound and the like which originally has a low water solubility, so the viscosity of the aqueous solution can be easily adjusted. The concentration and amount of the base used are not particularly limited.

When an aqueous solution of the produced fatty ester of isethionic acid or a salt thereof has problems such as staining and bad smells, sometimes treatment with hydrogen peroxide is effective. For example, the staining and smells can be ameliorated by adding 30% hydrogen peroxide to an aqueous solution of a salt of a fatty ester of isethionic in an amount of 0.01–1% followed by treatment at 50–100° C.

The obtained fatty ester of isethionic acid can be used for producing a salt of isethionic ester or as a reforming agent for various kinds of resins. The obtained salt of the isethionic acid fatty ester can be used for the same uses as those of the conventional processes. That means they can be used in various uses as an anionic surfactant. For example, they can be dissolved in a polar solvent, emulsified or dispersed to provide a synthesized soap, composite soap, shampoo, total body cleaning agent, fiber scouring agent, dyeing aid, rust proofing agent, lubricant, or resin reforming agent and the like. In particular, a salt of alkanolamine or ammonium salt are useful as main components in shampoos, and body cleaning agents. In the former case, the product shows improved blending properties, lathering properties and sensation after use, compared to products produced with the sodium salt.

EXAMPLES

The present invention will now be further illustrated by the following examples, however, the present invention is not limited to these examples so long as they do not exceed the essential features of the present invention.

Analysis of the reaction was conducted by a $^1$H-NMR method. That is to say, in the case of a fatty acid, signal of a methylene group adjacent to carbonyl carbon appears at $\delta 2.22$ ppm, while in the ester of the signal of a methylene group adjacent to carbonyl carbon appears at $\delta 2.29$ ppm. Therefore, the degree of conversion of a fatty acid was obtained from a sample dissolved in dimethyl sulfoxide (DMSO) by measuring the intensity of the signal at $\delta 2.22$ ppm and that at $\delta 2.29$ ppm using a JNM-LA400 type F-NMR apparatus produced by JEOL Ltd., and by calculating the intensity ratio of these signals. As for the degree of conversion of isethionic acid, since the signal of a methylene group adjacent to a sulfonate group appears at $\delta 2.72$ ppm in the isethionic acid, and at $\delta 2.82$ ppm in the ester, and the signal of a methylene group adjacent to oxygen atom appears at $\delta 3.69$ ppm (isethionic acid) and at $\delta 4.24$ ppm (ester), the degree of conversion of isethionic acid was obtained from the intensity ratio of these signals and a mean value was calculated.

The by-produced 2,2'-dithiodiethanol and the sulfoxide thereof were determined by a standard addition method using $^{13}$C-NMR and the sulfuric acid was determined by ion chromatography.

The polar solvent (water) solution of each salt of the fatty ester of isethionic acid was cooled until turbidity was observed, and then gradually reheated and the temperature at which the solution became transparent (clarifying temperature) was obtained by visual observation. The hue was inspected by visual observation. The smell was examined by an organoleptic test. The viscosity was measured using B type viscometer. Foaming properties were examined with a 0.2% aqueous solution at 50° C. by the Ross-Miles method.

In Table 1, the terms "immediately after" and "5 minutes after" mean that the foaming properties were measured "immediately after" and "5 minutes after" the preparation of a 0.2% aqueous solution of a salt which had been obtained by adding a base and water listed in each of the Tables. The unit of value is the height in mm of the foam.

Example 1

(1) 71.5% isethionic acid aqueous solution was obtained by oxidizing mercaptoethanol with hydrogen peroxide. The total amount of 2,2'-dithiodiethanol and a sulfoxide thereof obtained as by-products was 0.7%. The amount of sulfuric acid was 0.1%. Then 127 g of this 71.5% isethionic acid aqueous solution (0.72 mol of isethionic acid) and 144 g (0.72 mol) of lauric acid (neutralization value of 280 mgKOH/g) were added to a four-necked flask and heated under nitrogen stream to 100° C. This mixture was maintained at 100° C. for 30 minutes, and then the pressure was gradually reduced while taking the foaming state into consideration. There was little foaming, and it was possible to reduce the pressure from a normal pressure to 10–30 mmHg over about 30 minutes from the start of the pressure reduction. The water as the solvent and the water generated by esterification were removed under a reduced pressure of 10–30 mmHg for 2 hours to give a lauric ester of isethionic acid of the present invention.

The esterification reaction rate of the fatty acid in this example was 98%, and the esterification reaction rate of the isethionic acid was 97%.

(2) To the obtained reaction product, was added each base shown in Table 1 (Examples 1a–1h) and water such that the pH became 6.5 and the solid concentration became 30% to give an aqueous solution of each salt of lauric ester of isethionic acid of the present invention. The results of the measurements of the clarifying temperature, hue, smell and foaming properties of these products together with the bases added are shown in Table 1.

TABLE 1

| Example | Base | Clarifying temperature (° C.) | Hue APHA No | Smell* | Foaming property (mm) Immediately after | 5 min after |
|---|---|---|---|---|---|---|
| 1a | 28% ammonia aq. soln. | 15 | 150 | ± | 212 | 212 |
| 1b | Ethanolamine aq. soln. | 5 or below | 140 | ± | 223 | 223 |
| 1c | Triethanolamine aq. soln. | 5 or below | 130 | ± | 221 | 220 |
| 1d | Isopropanolamine aq. soln. | 5 or below | 140 | ± | 232 | 232 |
| 1e | Triisopropanolamine aq. soln. | 5 or below | 140 | ± | 220 | 220 |
| 1f | Ethylenediaminetetra (propylenegycol) aq. soln. | 5 or below | 130 | ± | 230 | 230 |
| 1g | Sodium hydroxide aq. soln. | gelled | — | ± | 212 | 204 |
| 1h | Potassium hydroxide aq. soln. | gelled | — | ± | — | — |

*Criteria for evaluation of smell
++: sensed strongly
+: sensed
±: barely sensed
—: not sensed Example 2

(1) 127 g of 71.5% isethionic acid aqueous solution (0.72 mol of isethionic acid) used in Example 1, 157 g (0.72 mol) of coconut oil fatty acid (neutralization value of 257 mgKOH/g) and 28 g of previously synthesized fatty ester of isethionic acid (10% based on the aqueous solution) were added to a four-necked flask. The mixture became homogeneous when stirred. The mixture was heated under a nitrogen stream to 80° C. and immediately after it reached 80° C., the pressure was gradually reduced while taking the foaming state into consideration. There was little foaming and it was possible to reduce the pressure from the normal pressure to 10–30 mmHg over about 30 minutes from the start of the pressure reduction. The water as the solvent and the water generated by esterification were removed under a reduced pressure of 10–30 mmHg for 3 hours to give a coconut oil fatty ester of isethionic acid.

Foaming during the dehydration reaction under the reduced pressure was much less than in the case of the after-mentioned Comparative Example 1, and the operation was able to be carried out easily. The esterification reaction rate of coconut oil fatty acid obtained from the reaction product by $^{1}$H-NMR method was 95%, the esterification reaction rate of isethionic acid was 95%.

(2) Then to the reaction product, was added each base shown in Table 2 (Examples 2a–2g) and water such that the resulting pH became 6.6 and the solid concentration became 31% to give an aqueous solution of each salt of coconut oil fatty ester of isethionic acid of the present invention. These were stained to some extent, and thus 30% hydrogen peroxide was added in an amount of 0.4% based on the aqueous solution and subjected to treatment at 80° C. The results of the measurements of the products obtained after the treatment together with the bases added are given in Table 2.

TABLE 2

| Example | Base | Clarifying temperature (° C.) | Hue APHA No | Smell | Foaming property (mm) | | Viscosity cPs |
| --- | --- | --- | --- | --- | --- | --- | --- |
| | | | | | Immediately after | 5 min after | |
| 2a | 28% ammonia aq. soln. | 15 | 250 | ± | 219 | 218 | 570 |
| 2b | Ethanolamine aq. soln. | 5 or below | 240 | ± | 224 | 224 | 9 |
| 2c | Triethanolamine aq. soln. | 5 or below | 230 | ± | 224 | 224 | 8 |
| 2d | Isopropanolamine. aq. soln. | 5 or below | 240 | ± | 228 | 228 | 10 |
| 2e | Triisopropanolamine aq. soln. | 5 or below | 240 | ± | 225 | 225 | 6 |
| 2f | Ethylenediaminetetra (propyleneglycol) aq. soln. | 5 or below | 230 | ± | 227 | 227 | 6 |
| 2g | Sodium hydroxide aq. soln. | gelled | — | ± | 216 | 216 | — |

Example 3

(1) 74.5% isethionic acid aqueous solution was obtained by oxidizing mercaptoethanol with hydrogen peroxide. The by-produced 2,2'-dithiodiethanol and a sulfoxide thereof was 1.3%, and sulfuric acid was 0.3%. The isethionic acid aqueous solution was subjected to stripping with nitrogen at 100° C. under 10–30 mmHg for 2 hours. To 122 g of this 74.5% isethionic acid aqueous solution (0.72 mol of isethionic acid) obtained after the stripping treatment, was added 144 g (0.72 mol) of lauric acid and the mixture was heated under nitrogen stream to 100° C. The mixture was maintained at 100° C. for 30 minutes, and then the pressure was gradually reduced while taking the foaming state into consideration. There was little foaming, and it was possible to reduce the pressure from a normal pressure to 10–30 mmHg over about 30 minutes from the start of the pressure reduction. The water as the solvent and the water generated by esterification were removed under a reduced pressure of 10–30 mmHg for 2 hours to give a lauric ester of isethionic acid.

The esterification reaction rate of the lauric acid obtained by $^1$H-NMR analysis of these reaction product was 95%, and the esterification reaction rate of the isethionic acid was 95%.

(2) To the obtained reaction product, were added a 28% ammonia aqueous solution and water such that the pH became 6.7 and the solid concentration became 32% to give an aqueous solution of ammonium salt of lauric ester of isethionic acid of the present invention. The clarifying temperature of the aqueous solution was 20° C.

Example 4

(1) 127 g of 71.5% the isethionic acid aqueous solution (0.72 mol of isethionic acid) used in Example 1, 225 g (0.79 mol) of oleic acid (neutralization value of 197 mgKOH/g) and 35 g of (previously synthesized) oleic ester of isethionic acid (10% based on the aqueous solution) were added to a four-necked flask. The mixture became homogeneous when stirred. The mixture was heated under a nitrogen stream to 70° C. and immediately after it reached 70° C., the pressure was gradually reduced while taking the foaming state into consideration. There was little foaming and it was possible to reduce the pressure from the normal pressure to 10–30 mmHg over about 30 minutes from the start of the pressure reduction. The water as the solvent and the water generated by esterification were removed under a reduced pressure of 10–30 mmHg for 4 hours to give an oleic ester of isethionic acid.

The esterification reaction rate of oleic acid obtained by $^1$H-NMR analysis of these reaction product was 93%, and the esterification reaction rate of isethionic acid was 90%.

(2) Then to the reaction product, were added a 28% ammonia aqueous solution and a water-ethanol (4:1) solution to give a water-ethanol (4:1) solution of ammonium salt of oleic ester of isethionic acid of the present invention.

Example 5

(1) To 127 g of the 71.5% isethionic acid aqueous solution (0.72 mol of isethionic acid) used in Example 1, was added 22 g of 28% ammonia aqueous solution (0.36 mol) with cooling for neutralization and a 50% ammonia neutralized product of isethionic acid was obtained. Then of 150 g (0.75 mol) of lauric acid was added thereto and the mixture was heated under nitrogen stream to 120° C. After the mixture reached 120° C., the pressure was gradually reduced while taking the foaming state into consideration. There was little foaming and it was possible to reduce the pressure from a normal pressure to 10–30 mmHg over about 30 minutes from the start of the pressure reduction. The water as the solvent and the water generated by esterification were removed under a reduced pressure of 10–30 mmHg for 2 hours to give a partial ammonium salt of a lauric ester of isethionic acid. The esterification reaction rate of lauric acid obtained by $^1$H-NMR analysis of the reaction product was 94%, and the esterification reaction rate of isethionic acid was 97%.

(2) Then, to the reaction product, were added a 28% ammonia aqueous solution and water such that the pH became 6.7 and the solid concentration became 31%, to give an aqueous solution of ammonium salt of lauric ester of isethionic acid. The clarifying temperature of the aqueous solution was 17° C. The hue was APHA No. 150.

Comparative Example 1

To 122 g (0.69 mol) of the 71.5% isethionic acid aqueous solution used in Example 1, was added 42 g of 28% ammonia aqueous solution (0.69 mol) and the pH was adjusted to 5 to give an ammonium salt of isethionic acid. To this mixture, were added 151 g (0.69 mol) of the coconut oil fatty acid used in Example 2, 0.25 g of methanesulfonic acid as a catalyst, and 0.42 g of hypophosphorous acid, and the mixture was heated to 130° C. under nitrogen stream and the pressure was gradually reduced while taking the foaming state into consideration. vigorous foaming occurred and it was difficult to reduce the pressure below 140–150 mmHg even 60 minutes after the start of the pressure reduction and it took 10 hours for the pressure to reach 10–30 mmHg.

Comparative Example 2

An ammonium salt of isethionic acid, coconut oil fatty acid, methanesulfonic acid, and hypophosphorous acid were mixed in a manner similar to that used in Comparative Example 1, and the mixture was heated to 170° C. under nitrogen stream and the pressure was gradually reduced while taking the foaming state into consideration. Vigorous foaming occurred and it was difficult to reduce the pressure below 140–150 mmHg even 60 minutes after the start of the pressure reduction. The reaction was continued for 5 more hours at a reduced pressure of around 100–140 mmHg. The water generated was removed under a reduced pressure of 100–140 mmHg for 3 hours and an ammonium salt of coconut oil fatty ester of isethionic acid was synthesized. The esterification reaction rate of coconut oil fatty acid obtained by $^1$H-NMR analysis of the reaction product was 83%.

Then 28% ammonia aqueous solution and water were added to the reaction product such that the pH became 6.9 and the solid content became 32%, and 30% hydrogen peroxide was added in an amount of 0.1% based on the aqueous solution and the mixture was subjected to treatment at 60° C. for 3 hours. The results obtained after the treatment are shown in Table 3. The hue of the aqueous solution was Gardner No.5, and the hue and the smell were ameliorated by the treatment to some extent, however, the hue was inferior and the smell was stronger than those of Example 2. The process of the present invention provides a better hue and smell as shown by comparison with this Comparative Example.

TABLE 3

|  | Base | Clarifying temperature (° C.) | Hue | Smell |
| --- | --- | --- | --- | --- |
| Example |  |  |  |  |
| 2a | 28% ammonia aq.soln, | 13 | APHA No250 | ± |
| Comparative Example |  |  |  |  |
| 2 | 28% ammonia aq.soln, | 60 or above | Gardner No5 | + + |
| 3 | 28% ammonia aq.soln, | 60 or above | Gardner No5 | + + |
| 4 | 28% ammonia aq.soln, | 60 or above | Gardner No4 | + + |

Comparative Example 3

122 g (0.72 mol) of the 74.5% isethionic acid aqueous solution used in Example 3 and 166 g (0.76 mol) of coconut oil fatty acid were added to a four-necked flask and heated under a nitrogen stream to 160° C. After reaching 160° C., the pressure was gradually reduced and the water generated was removed under a reduced pressure of 10–30 mmHg by distillation and a coconut oil fatty ester of isethionic acid was synthesized. The esterification reaction rate of coconut oil fatty acid obtained by $^1$H-NMR analysis of the reaction product was 84%. A 28% ammonia aqueous solution and water were added to the reaction product such that the pH became 6.7 and the solid content became 31% to adjust the aqueous solution. The clarifying temperature of the aqueous solution was over 60° C. and the hue of the aqueous solution was Gardner No.5. As shown by comparison with this Comparative Example, the process of the present invention provides excellent hue and smell.

Comparative Example 4

157 g (0.72 mol) of coconut oil fatty acid was heated to 110° C. and brought under a reduced pressure (50–70 mmHg) by use of water jet vacuum pump. Then, 127 g (0.72 mol) of the 71.5% isethionic acid used in Example 1 was added thereto dropwise and the mixture was stirred at 110° C. for 30 minutes and at 135° C. for 30 minutes while the solvent and the water resulting from reaction were removed by evaporation to give a fatty ester of isethionic acid. Foaming during the dehydration reaction under a reduced pressure was nearly the same level as that of each Example, but the esterification reaction rate of the coconut oil fatty acid obtained by $^1$H-NMR analysis of the reaction product was 79%.

To the obtained reaction product, was added a 28% ammonia aqueous solution and water such that the resulting pH became 6.8 and the solid concentration became 32% to give an ammonium salt of coconut oil fatty ester of isethionic acid. The obtained aqueous solution had a clarifying temperature of over 60° C. and a hue of Gardner No.4. As shown by comparison with this Comparative Example the process of the present invention provides excellent clarifying temperature and hue.

INDUSTRIAL APPLICABILITY

The present invention provides a process of preparing a fatty ester of isethionic acid or a salt thereof, and a polar solvent solution of the salt of the fatty ester of isethionic acid, having excellent solubility in polar solvents, and salts of various counter ions can be produced therewith, wherein reaction is carried out under mild conditions and accordingly few by-products are yielded, the hue and the smell are ameliorated, little foaming occurs and since the dehydration of the reaction system under a reduced pressure can be carried out easily, the reaction time can be shortened.

What is claimed is:

1. A process for preparing a salt of acyloxy alkanesulfonic acid, comprising:

reacting a fatty acid and/or an alkyl ester of a fatty acid and a hydroxy alkylsulfonic acid in an esterification reaction at a maximum temperature of not more than 130° C., thereby providing an acyloxy alkanesulfonic acid;

reacting said acyloxy alkanesulfonic acid with ethylenediamine tetra(propyleneglycol).

2. The process according to claim 1, wherein the esterification reaction is carried out at a reduced pressure of not more than 30 mmHg.

3. The process according to claim 1, wherein said hydroxy alkylsulfonic acid is 2-hydroxy ethanesulfonic acid.

4. The process according to claim 1, wherein a molar ratio of said fatty acid and/or said alkyl ester of said fatty acid to said hydroxy alkylsulfonic acid is from 0.95 to 1.1.

5. The process according to claim 1, further comprising adding a fatty acid ester of 2-hydroxy alkanesulfonic acid or a salt thereof which is prepared beforehand before said reacting of said fatty acid and/or alkyl ester of a fatty acid and said hydroxy alkylsulfonic aczid.

6. The process according to claim 1, wherein said reacting with ethylenediamine tetra(propyleneglycol) is carried out in a polar solvent.

7. The process according to claim 6, wherein said polar solvent is selected from the group consisting of water, a lower alcohol, a glycol, glycerin and mixtures thereof.

8. The process according to claim 6, wherein said polar solvent has a pH of 6 to 8.

9. A water soluble salt of an acyloxy alkanesulfonic acid obtained by the process according claim 1.

10. A surfactant, comprising:

a salt of an acyloxy alkanesulfonic acid obtained by the process according claim 1.

11. A polar solvent solution, emulsion or dispersion of a salt of an acyloxy alkanesulfonic acid obtained by the process according claim 1.

12. A process for preparing a salt of an acyloxy alkanesulfonic acid, comprising:

reacting a fatty acid and/or an alkyl ester of a fatty acid and a hydroxy alkylsulfonic acid in an esterification reaction at a maximum temperature of not more than 130° C., thereby providing an acyloxy alkanesulfonic acid;

reacting said acyloxy alkanesulfonic acid with a base in water, glycerin or a combination thereof.

13. The process according to claim 12, wherein the esterification reaction is carried out at a reduced pressure of not more than 30 mmHg.

14. The process according to claim 12, wherein said hydroxy alkylsulfonic acid is 2-hydroxy ethanesulfonic acid.

15. The process according to claim 12, wherein said base is an alkanol amine.

16. The process according to claim 15, wherein said alkanol amine is ethylenediamine tetra(propyleneglycol).

17. The process according to claim 12, wherein said water, glycerin or said combination thereof has a pH of 6 to 8.

18. A water soluble salt of an acyloxy alkanesulfonic acid obtained by the process according claim 12.

19. A surfactant, comprising:

a salt of an acyloxy alkanesulfonic acid obtained by the process according claim 12.

20. A polar solvent solution, emulsion or dispersion of a salt of an acyloxy alkanesulfonic acid obtained by the process according claim 12.

21. A process for preparing an acyloxy alkanesulfonic acid, comprising:

reacting a fatty acid and/or an alkyl ester of a fatty acid and a hydroxy alkylsulfonic acid in an esterification reaction at a maximum temperature of not more than 130° C., in the presence of a fatty acid ester of 2-hydroxy alkanesulfonic acid or a salt thereof which is prepared beforehand.

22. The process according to claim 21, wherein said fatty acid ester of 2-hydroxy alkanesulfonic acid or said salt thereof is added in an amount of 5–20% based on the total weight of said fatty acid and/or alkyl ester of said fatty acid and said hydroxy alkylsulfonic acid.

23. The process according to claim 21, wherein the esterification reaction is carried out at a reduced pressure of not more than 30 mmHg.

24. The process according to claim 21, wherein the hydroxy alkylsulfonic acid is 2-hydroxy ethanesulfonic acid.

25. A process for preparing a salt of acyloxy alkanesulfonic acid comprising:

reacting the acyloxy alkanesulfonic acid prepared according to the process of claim 21 with a base.

26. The process according to claim 25, wherein said base is an alkanol amine.

27. The process according to claim 26, wherein said alkanol amine is ethylenediamine tetra(propyleneglycol).

28. The process according to claim 25, wherein said reacting with said base is carried out in a polar solvent.

29. The process according to claim 28, wherein said polar solvent has a pH of 6 to 8.

30. The process according to claim 28, wherein said polar solvent is selected from the group consisting of water, a lower alcohol, a glycol, glycerin and a mixture thereof.

31. A water soluble salt of acyloxy alkanesulfonic acid obtained by the process according to claim 25.

32. A surfactant, comprising:

a salt of an acyloxy alkanesulfonic acid obtained by the process according to claim 25.

33. A polar solvent solution, emulsion or dispersion of a salt of an acyloxy alkanesulfonic acid obtained by the process according to claim 25.

* * * * *